United States Patent [19]
Sunami et al.

[11] Patent Number: 5,368,860
[45] Date of Patent: Nov. 29, 1994

[54] PREPARATION FOR TRANSDERMAL DRUG ADMINISTRATION

[75] Inventors: Masaki Sunami, Yokohama; Koji Maruyama, Ibaraki; Mitsuhiko Hori, Ibaraki; Shoichi Tokuda, Ibaraki; Kenichiro Saito, Osaka; Ikuo Kishi, Ichikawa, all of Japan

[73] Assignee: Nitto Denko Corporation, Tokyo, Japan

[21] Appl. No.: 798,149

[22] Filed: Nov. 26, 1991

[30] Foreign Application Priority Data

Nov. 30, 1990 [JP] Japan ................................ 2-338885

[51] Int. Cl.⁵ .............................................. A61F 13/02
[52] U.S. Cl. .................................. 424/448; 424/443; 424/449
[58] Field of Search ........................ 424/448, 449, 443

[56] References Cited

U.S. PATENT DOCUMENTS

| | | | |
|---|---|---|---|
| 4,655,768 | 4/1987 | Marecki et al. | 424/448 |
| 5,120,325 | 6/1992 | Dow, Jr. | 604/304 |

FOREIGN PATENT DOCUMENTS

| | | |
|---|---|---|
| 0156080 | 10/1985 | European Pat. Off. |
| 0331392 | 9/1989 | European Pat. Off. |
| WO8911872 | 12/1989 | European Pat. Off. |
| 0393727 | 10/1990 | European Pat. Off. |

OTHER PUBLICATIONS

Chemical Abstract, vol. 100, No. 2, p. 371 (1984).
Chemical Abstract, vol. 100, No. 2, pp. 306–307, (1984).
Eurpean Search Report, Nov. 26, 1992.

Primary Examiner—Thurman K. Page
Assistant Examiner—Leon R. Horne
Attorney, Agent, or Firm—Sughrue, Mion, Zinn, Macpeak & Seas

[57] ABSTRACT

A preparation for transdermal drug administration comprising a flexible backing layer and a pressure-sensitive adhesive layer containing a local anesthetic in a proportion of 40–65 weight %. Since the ratio of the amount of the undissolved local anesthetic (Ac) to that of the dissolved local anesthetic (As), Ac/As, in the pressure-sensitive adhesive layer is determined to be in the range of 0.1–1.8, the preparation for transdermal drug administration of the present invention is superior in self-adhesiveness and leaves no adhesive material upon removal from the skin. In addition, burst-like release of the undissolved drug from the pressure-sensitive adhesive layer immediately after application to the skin permits rapid appearance of the anesthetic effect, which enables wide clinical application of the preparations of the present invention.

3 Claims, No Drawings

PREPARATION FOR TRANSDERMAL DRUG ADMINISTRATION

BACKGROUND OF THE INVENTION

The present invention relates to a preparation for a transdermal drug administration that contains a local anesthetic as a medicinal ingredient.

Various preparations for transdermal administration of a local anesthetic, and some of them have been marketed as liquid- or ointment-form external preparations. However, application of these preparations to the common integument poses problems, such as difficulty in controlling the dose, possibility of staining clothes, and so on.

Although an analgesic composition, retains the drug at a local site longer (Japanese Patent Publication No. 130540/1988), such a composition falls within the category of liquid or ointment preparations intended for administration to mucous membrane, which is not entirely suitable for application to the common integument.

Japanese Patent Publication No. 272521/1989 teaches a patch preparation for application to the gum. This preparation overcomes disadvantages of conventional liquid or ointment preparations and can be handled easily. Still, this preparation is unsuitable for application to the common integument since it is originally designed for application to the gum; the application site must have adequate moisture in order to tightly secure the preparation to the site.

Also, an adhesive tape preparation for a transdermal administration of a local anesthetic (Japanese Patent Publication No. 299215/1989), offers easy application and easy control over the dose. Its self-adhesive matrix comprises an adhesive material selected from among the group of poly(styrene-butadiene) block copolymer, poly(styrene-isoprene-stylene) block copolymer, high molecular weight polyisobutylene polymer, low molecular weight polyisobutylene polymer and ethylene-vinyl acetate copolymer. Yet, such polymers or copolymers do not result in the rapid appearance of the anesthetic effect, which is one of the desired properties of a local anesthetic. Moreover, its self-adhesive matrix comprises an adhesion-imparting agent, a fluidity-imparting agent, and an antioxidant as a medicinal ingredients in addition to a local anesthetic. This is not only uneconomical, but also pharmaceutically unstable because of the potential reactions between those agents and the primary medicinal ingredient.

Japanese Patent Publication No. 185713/1985 teaches a preparation for transdermal drug administration in which a transdermally absorbable drug is dispersed as recrystallized fine powder in a pressure-sensitive adhesive macromolecule copolymer. This percutaneously absorbable drug is contained in an amount corresponding to at least 1.2 times the saturation solubility of the pressure-sensitive adhesive macromolecule copolymer. This preparation is easily handled and better controls the dose. Yet, according to the preparation's description, the amount of the transdermally absorbable drug relative to the pressure-sensitive adhesive macromolecule copolymer is 40 weight % or less, an amount that hinders a rapid anesthetic effect. For a rapid effect, it is necessary for the drug to be suddenly released or burst upon initial application; this drug release and the adhesion to the skin depend on the proportional amount of the dissolved drug to the undissolved drug in the pressure-sensitive adhesive macromolecule copolymer. However, this cited patent neither teaches or suggests this.

SUMMARY OF THE INVENTION

The present inventors conducted intensive studies to resolve the problems of transdermal drug preparations mentioned above. As a result, they discovered that with a preparation for transdermal drug administration comprising a flexible backing layer and a pressure-sensitive adhesive layer formed thereon containing a local anesthetic, the drug release and absorbability via the skin are greatly influenced by the concentration of the local anesthetic in the pressure-sensitive adhesive layer, the ratio of the amount of the dissolved local anesthetic (As) to that of the undissolved local anesthetic (Ac) contained therein, and the type of the pressure-sensitive adhesive to be used.

Then, the inventors created the preparation for a transdermal drug administration of the present invention wherein the amount of local anesthetic is within a certain range in a specific pressure-sensitive adhesive. It exhibits excellent local anesthetic effect and adhesion to the skin, as well as ease in handling.

That is, the present invention relates to a preparation comprising a flexible backing layer and a pressure-sensitive adhesive layer formed on the backing layer, wherein ① a local anesthetic is contained in the pressure-sensitive adhesive layer in a proportion of 40–65 weight % and the ratio of the amount of the undissolved local anesthetic (Ac) to that of the dissolved local anesthetic (As), Ac/As, is in the range of from 0.1 to 1.8, and ② an acrylate adhesive is used as the pressure-sensitive adhesive.

DETAILED DESCRIPTION OF THE INVENTION

The details of the present invention follow below.

The backing layer used in the present invention is not limited as long as it is flexible and impervious to drugs. Examples thereof include: films and sheets made of polyolefin, polyester, poly(vinyl alcohol), poly(vinyl chloride), poly(vynilidene chloride), polyamide, polytetrafluoroethylene, etc.; deposited metal films and sheets; and laminated sheets using two kinds or more thereof, which are about 500 μm or less, preferably 5-150 μm in thickness.

The pressure-sensitive adhesive layer of the present invention contains and sustains the local anesthetic in a proportion of 40–65 weight %, and releases the drug quickly to promote absorption via the skin, while securing the preparation of the present invention tightly onto the skin.

In the present invention, the pressure-sensitive adhesive is preferably an acrylic pressure-sensitive adhesive of a copolymer of (meth)acrylic acid alkyl ester and (meth)acrylic acid because of its adhesion to the skin, stability with the local anesthetic to be used, and rapid migration and absorption of the local anesthetic from the adhesive layer to and by the skin.

Examples of the (meth)acrylic acid alkyl ester for forming said acrylic pressure-sensitive adhesive include copolymers of one or more of (meth)acrylic acid alkyl esters having an alkyl of 4 to 13 carbon atoms, such as butyl (meth)acrylate, pentyl (meth)acrylate, hexyl (meth)acrylate, heptyl (meth)acrylate, octyl (meth)acrylate, nonyl (meth)acrylate, decyl (meth) acrylate, undecyl (meth)acrylate, dodecyl (meth)acrylate and tridecyl (meth)acrylate.

The (meth)acrylic acid alkyl ester of the present invention encompasses various isomers whose alkyl moiety is straight or branched and various isomers having different substitution sites and their derivatives.

Such acrylic pressure-sensitive adhesives have a high degree of polymerization, improved cohesiveness and adhesiveness, and permit stable retention of large amount of local anesthetics, and migration of the local anesthetic to the skin shortly after application.

It is desirable that the weight ratio of (meth)acrylic acid alkyl ester to (meth)acrylic acid contained in the acrylic pressure-sensitive adhesive be 65/35-99/1 in view of the balance between the adhesiveness to the skin and cohesiveness.

In preparing said acrylic pressure-sensitive adhesive, another monomer may optionally replace a part of the above-mentioned monomers for the copolymerization as long as the efficacy of the drug and the adhesiveness to the skin are not impaired. Examples thereof include vinyl acetate, (meth) acrylic acid hydroxyalkyl ester, (meth)acrylic acid alkoxyalkyl ester, (meth)acrylic acid alkylaminoalkyl ester, (meth) acrylamide, derivatives thereof, N-vinylpyrrolidone and (meth) acrylonitrile.

The proportioned amount of the local anesthetic to be contained in the above-mentioned pressure-sensitive adhesive layer should be 40-65 weight %, and the ratio of the amount of the undissolved local anesthetic (Ac) to that of the dissolved local anesthetic (As), Ac/As, within the pressure-sensitive adhesive layer should be within the range of 0.1-1.8. Note that the undissolved local anesthetic means the crystalline precipitate or dispersed drug resulting from addition beyond the saturation solubility in the adhesive polymer, and the dissolved local anesthetic means the drug existing in molecule dispersion or noncrystalline state in the polymer, which can be confirmed by a microscope examination or X-ray diffractometry. When the Ac/As is below 0.1, the local anesthetic acts like a plasticizer to the acrylic adhesive in the pressure-sensitive adhesive layer of the present invention, resulting in gooey threads from the pressure-sensitive adhesive layer upon removal from the skin after application. This in turn results in remains of the pressure-sensitive adhesive layer, either partially or entirely over the applied site on the skin, staining of the common integument, and delayed local anesthetic effect. On the other hand, when the Ac/As exceeds 1.8, self-adhesion of the pressure-sensitive adhesive layer decreases so that the layer cannot be adhered to the skin.

Where the Ac/As is in the range of 0.1-1.8, most favorably 0.6 or above, the local anesthetic is in part undissolved in the pressure-sensitive adhesive layer, which contributes to the improved cohesiveness of the pressure-sensitive adhesive. In addition, the presence of the undissolved local anesthetic in a rather large amount leads to a burst of drug release shortly after application, causing prompt migration of the drug in an amount necessary for an anesthetic effect, all of which assures a rapid appearance of the anesthetic effect, which is expected of a local anesthetic.

While the amount of the local anesthetic to be contained in the pressure-sensitive adhesive layer is determined to be in the range of from 40 to 65 weight %, it is preferably not less than 45 weight % to ensure the rapid appearance of the effect.

The local anesthetic to be used in the present invention is selected from among amide anesthetics and ester anesthetics, and preferably selected from among cocaine, procaine, chloroprocaine, tetracaine, lidocaine, mepivacaine, prilocaine, bupivacaine and dibucaine.

The preparation of the present invention contains one or more of the above-mentioned local anesthetics in the pressure-sensitive adhesive layer.

The thickness of the pressure-sensitive adhesive layer containing local anesthetic is preferably in the range of from 5 to 30 μm to promote cost effective and rapid drug administration.

The preparation of the present invention has components described above, as well as a local anesthetic in a proportion of 40-65 weight % within the pressure-sensitive adhesive layer. Since the ratio of the amount of the undissolved local anesthetic (Ac) to that of the dissolved local anesthetic (As), Ac/As, in the pressure-sensitive adhesive layer is determined to be in the range of 0.1-1.8, the preparation of the present invention is extremely self-adhesive and leaves no adhesive material upon removal from the skin. In addition, a burst-like release of the undissolved drug from the pressure-sensitive adhesive layer immediately after application to the skin permits rapid appearance of the local anesthetic effect, which makes it possible to be utilized for the pre-operational treatment of needle indwelling in a vein or an artery, dura or lumbar puncture, arthrocentesis and minor dermic operation. As a result, patients' pain can be vastly reduced, which can lead to many clinical applications.

The present invention is hereinbelow described in detail illustrative working examples. The present invention is not strictly limited to these examples, but can be modified in various manners.

In the following description, part(s) and % refer to part(s) by weight and weight %, respectively.

EXAMPLE 1

2-Ethylhexyl acrylate (95 parts) and acrylic acid (5 parts) were charged in a flask under an inert gas atmosphere and azobisisobutyronitrile (0.3 part) was added thereto as a polymerization initiator. The polymerization was conducted in ethyl acetate while maintaining the temperature at 60° C. to give the acrylic pressure-sensitive adhesive solution A (solids: 41.2%).

Thereto was added lidocaine in a ratio of 60 parts thereof relative to 40 parts of the solids, after which ethyl acetate was added to produce a solution containing 35% solids. The thus-obtained solution was coated on a polyester release paper to form a 20 μm thickness after drying, which was then dried at 100° C. for 5 minutes to form a pressure-sensitive adhesive layer containing 60% lidocaine. After the obtained pressure-sensitive adhesive layer containing 60% lidocaine was adhered onto a 12 μm-thick polyester backing layer, it was allowed to stand at room temperature for 24 hours to crystallize the lidocaine in the pressure-sensitive adhesive layer, by which a preparation of the present invention was obtained (Ac/As was about 1.6).

EXAMPLE 2

To the acrylic pressure-sensitive adhesive solution A used in Example 1 was added lidocaine in a ratio of 40 parts thereof relative to 60 parts of the solids to give a solution containing 30% solids.

The obtained solution was treated in the same manner as in Example 1, resulting in a preparation of the present invention (Ac/As was about 0.7).

EXAMPLE 3

To the acrylic pressure-sensitive adhesive solution A used in Example 1 was added lidocaine in a ratio of 50 parts thereof relative to 50 parts of the solids, and ethyl acetate was further added to give a solution containing 33% solids.

The obtained solution was treated in the same manner as in Example 1, resulting in a preparation of the present invention (Ac/As was about 1.2).

COMPARATIVE EXAMPLE 1

To the acrylic pressure-sensitive adhesive solution A used in Example 1 was added lidocaine in a ratio of 70 parts thereof relative to 30 parts of the solids, and ethyl acetate was further added to give a solution containing 30% solids.

The obtained solution was treated in the same manner as in Example 1 to give a preparation containing a local anesthetic (Ac/As was about 2.0).

COMPARATIVE EXAMPLE 2

To the acrylic pressure-sensitive adhesive solution A as used in Example 1 was added lidocaine in a ratio of 20 parts thereof relative to 80 parts of the solids, and ethyl acetate was further added to give a solution containing 25% solids.

The obtained solution was treated in the same manner as in Example 1 to give a preparation containing a local anesthetic (Ac/As was 0).

REFERENCE EXAMPLE 1

Carboxyvinyl polymer (Wako Junyaku Kogyo, Hibis Waco 105, 2.6 weight %), ethanol (40 weight %) and purified water (47.4 weight %) were mixed thoroughly to dissolve the carboxyvinyl polymer. Thereto was added lidocaine (10 weight %), and the mixture was mixed to dissolve lidocaine, by which there was obtained a gel ointment containing lidocaine.

EXPERIMENT EXAMPLE 1

A 3.17×3.17 (10 cm$^2$) specimen cut out from each of the preparations obtained in Examples 1–3 and Comparative Examples 1 and 2, was adhered onto the human inner forearm for 30 minutes. The adhesion, remaining adhesive material upon removal from the skin, and anesthetic effect were examined. The effect was examined by the pin pricking method. That is, after 30 minutes of adhesion, the specimen was removed and an intracutaneous pin was pricked on the applied area to determine the degree of pain, based on a numerical evaluation of the anesthetic effect made according to evaluation criteria.

As to the Reference Example, 0.1 g of the lidocaine-containing gel ointment obtained therein was applied onto an area of 3.15×3.15 cm on a human inner forearm, and a similar experiment was conducted.

| Anesthetic effect evaluation criteria |
| --- |
| 0: no pain was sensed on 5 points. |
| 1: pain was sensed on 1 of 5 points. |
| 2: pain was sensed on 2 of 5 points. |
| 3: pain was sensed on 3 of 5 points. |
| 4: pain was sensed on 4 of 5 points. |
| 5: pain was sensed on 5 points. |

The results are summarized in Table 1.

TABLE 1

| | Adhesiveness to the skin | Adhesive material remaining on the skin | Anesthetic effect |
| --- | --- | --- | --- |
| Example 1 | ○ | none | 0.9 |
| Example 2 | ○ | partial remainder around the adhesion site | 1.6 |
| Example 3 | ○ | none | 1.1 |
| Comp. Ex. 1 | X | adhesion unattainable due to the residual adhesive material on the release paper | — |
| Comp. Ex. 2 | ○ | Remainder on the entire site | 3.1 |
| Ref. Ex. | — | — | 4.1 |

○: good adhesion
X: adhesion unattainable
Note that the anesthetic effect of the Reference Example was 1.9 after 3 hours' application.

What is claimed is:

1. A preparation for transdermal drug administration comprising a flexible backing layer and a pressure-sensitive adhesive layer composed of a copolymer of (meth-)acrylic acid alkyl ester and (meth)acrylic acid and containing a local anesthetic in a proportion of 40–65% by weight based on the total weight of the pressure-sensitive adhesive layer, wherein the ratio of the amount of the undissolved local anesthetic (Ac) to that of the dissolved local anesthetic (As), Ac/As, is 0.1–1.8.

2. A preparation for transdermal drug administration according to claim 1, wherein the local anesthetic is at least one member selected from the group consisting of cocaine, procaine, chloroprocaine, tetracaine, lidocaine, mepivacaine, prilocaine, bupivacaine, dibucaine and their pharmacologically acceptable salts.

3. A preparation for transdermal drug administration according to claim 1, wherein the acrylic pressure-sensitive adhesive is obtained by polymerization of 65–99 weight % of (meth)acrylic acid alkyl ester and 1–35 weight % of (meth)acrylic acid.

* * * * *

UNITED STATES PATENT AND TRADEMARK OFFICE
CERTIFICATE OF CORRECTION

PATENT NO. : 5,368,860
DATED : November 29, 1994
INVENTOR(S) : SUNAMI et al.

It is certified that error appears in the above-identified patent and that said Letters Patent is hereby corrected as shown below:

On the Title page, item [73] Assignee should read
--Nitto Denko Corporation, Tokyo, Japan and Lederle (Japan), Ltd., Tokyo, Japan--.

Signed and Sealed this

Twentieth Day of February, 1996

Attest:

Attesting Officer

BRUCE LEHMAN
Commissioner of Patents and Trademarks